US010752571B2

United States Patent
Pillai et al.

(10) Patent No.: US 10,752,571 B2
(45) Date of Patent: Aug. 25, 2020

(54) METHOD FOR PURIFICATION OF 4-HYDROXYACETOPHENONE

(71) Applicants: SYMRISE AG, Holzminden (DE); SINO-HIGH (CHINA) CO. LTD., Nanjing (CN)

(72) Inventors: Ravikumar Pillai, Mahwah, NJ (US); Sven Siegel, Höxter (DE); Ev Suess, Bevern (DE); Karolin Bolte, Boffzen (DE); Yan Liuxin, Nanjing (CN)

(73) Assignees: SYMRISE AG, Holzminden (DE); SINO-HIGH (CHINA) CO. LTD., Nanjing (CN)

( * ) Notice: Subject to any disclaimer, the term of this patent is extended or adjusted under 35 U.S.C. 154(b) by 0 days.

(21) Appl. No.: 16/337,467

(22) PCT Filed: Apr. 21, 2017

(86) PCT No.: PCT/EP2017/059489
§ 371 (c)(1),
(2) Date: Mar. 28, 2019

(87) PCT Pub. No.: WO2018/068902
PCT Pub. Date: Apr. 19, 2018

(65) Prior Publication Data
US 2020/0039911 A1 Feb. 6, 2020

(30) Foreign Application Priority Data
Oct. 14, 2016 (CN) .......................... 2016 1 0900121

(51) Int. Cl.
C07C 45/81 (2006.01)
C07C 45/79 (2006.01)
C07C 49/825 (2006.01)

(52) U.S. Cl.
CPC .............. *C07C 45/81* (2013.01); *C07C 45/79* (2013.01); *C07C 49/825* (2013.01)

(58) Field of Classification Search
CPC ................................ C07C 45/79; C07C 45/81
See application file for complete search history.

(56) References Cited

FOREIGN PATENT DOCUMENTS

| CN | 102093189 A | 6/2011 |
|---|---|---|
| CN | 104490716 A | 4/2015 |

OTHER PUBLICATIONS

International Search Report and Written Opinion dated Jun. 26, 2017 for corresponding PCT Application No. PCT/EP2017/059489.
Bernardes, Carlos E.S. et al., "Polymorphism in 4'-Hydroxyacetophenone: Structure and Energetics," Crystal Growth & Design, vol. 8, No. 7, 2008, pp. 2419-2430 XP002771038.
Wilson, Noel S. et al., "Mild Base Mediated Desilylation of Various Phenolic Silyl Ethers," Tetrahedron Letters, vol. 38, No. 2, 1997, pp. 187-190 XP004070499.
Chenthamarai, S. et al., "Growth and single crystal XRD characterization of undoped and doped 4-hydroxyacetophenone," Crystal Engineer, Elsevier Science Publishers, Barking, GB, vol. 4, No. 1, 2001, pp. 37-48 XP004250121.

*Primary Examiner* — Sikarl A Witherspoon
(74) *Attorney, Agent, or Firm* — Polsinelli PC

(57) ABSTRACT

Methods of purifying crude 4-hydroxyacetophenone using one or more solvents as well as products comprising or consisting of crystallized 4-hydroxyacetophenone and one, two or more solvent(s). The products may be obtained or obtainable from the methods for purifying crude 4-hydroxyacetophenone.

20 Claims, 2 Drawing Sheets

METHOD FOR PURIFICATION OF 4-HYDROXYACETOPHENONE

CROSS-REFERENCE TO RELATED APPLICATIONS

This application is a national stage application (under 35 U.S.C. § 371) of PCT/EP2017/059489, filed Apr. 21, 2017, which claims benefit of priority of Chinese Application No. 201610900121.0, filed Oct. 14, 2016, which are incorporated herein by reference in their entireties.

FIELD OF THE INVENTION

The present invention primarily relates to a method of purifying crude 4-hydroxyacetophenone. The present invention furthermore relates to a product comprising or consisting of crystallized 4-hydroxyacetophenone and one, two or more solvent(s) as defined herein, the product being obtained or obtainable by a method as defined herein.

Further aspects of the present invention will arise from the description below, in particular from the examples, as well as from the attached patent claims.

4-Hydroxyacetophenone can be used as a pharmaceutical intermediate in the synthesis of drugs such as Paracetamol, Ractopamine and Atenolol. It can also be used as a raw material for cosmetics, and was, for example, embodied in the Used Cosmetics Raw Material Catalogue by the China Food and Drug Administration (CFDA).

When used in cosmetics, 4-hydroxyacetophenone has the following advantageous characteristics:
(a) It has a certain anticorrosion ability,
(b) it has great ability to kill *Aspergillus brasiliensis*, and
(c) it has a certain ability to restrain *Pseudomonas aeruginosa* (Daily Chemical Industry: 2015, 45:269).

In CN104490716 it is disclosed that when 4-hydroxyacetophenone is formulated with 1,2-hexanediol and the Chinese herbal medicine specified therein, 4-hydroxyacetophenone displays excellent anticorrosion ability and at the same time does not cause any harm to a person's skin. Thus, 4-hydroxyacetophenone is an excellent substitute for such preservatives used in pharmaceutical or cosmetic compositions that have a detrimental effect on the human skin.

The standard synthesis of 4-hydroxyacetophenone starts from phenol, which is converted to phenyl acetate by esterification reaction. Phenyl acetate is then converted into 4-hydroxyacetophenone in a rearrangement reaction.

The commercial grade material has a strong odor and color and high phenol content of 100 ppm to 1000 ppm making it unsuitable for cosmetic applications without further purification.

The purification of crude 4-hydroxyacetophenone is usually carried out by means of one of the following methods:
(a) Recrystallization from water (as disclosed in CN102093189A)
(b) Purification by column chromatography (as disclosed in J. Org. Chem., 2011, 76(7):2296-2300).

The drawbacks of using purification method (a), i.e. using water as the solvent in the recrystallization step, are that the used amount of water is very large (usually about 15 to 20 times of the quantity of the raw material) and the solubility of the crude 4-hydroxyacetophenone in water is low, resulting in a low working efficiency for this method. Moreover, recrystallization of 4-hydroxyacetophenone from water usually results in a powder, not a crystallized product, which has bad flowability, is easy to cake and inconvenient to use. If the water is used repeatedly, the content of salt and phenols contained therein will increase continuously. This results in a negative effect on the product quality and high costs for this post-treatment method. Lastly, the color of the final product is darker and thus less attractive to the customer or consumer if small amounts of residual water remain inside the final product.

The drawbacks of using purification method (b), i.e. column chromatography, is that the sample volume that can be purified is limited because of the column length. Thus, this method only is suitable when the sample quantity is small. Moreover, this chromatographic method is quite involved and the solvent volume used is large. Thus, the associated costs are very high and this method is not suitable for industrialization.

Consequently, both of the purification methods described above are not suitable for application on industrial scale, because of the high costs associated with them and their low production efficiency.

BRIEF SUMMARY OF THE INVENTION

Therefore, it was an object of the present invention to provide a purification method for crude 4-hydroxyacetophenone that yields a highly pure, crystalline, colorless and odorless solid with superior (water) solubility and flowability properties and a very low residual content of the precursor phenol. It was a further object of the invention to provide a purification method for 4-hydroxyacetophenone that is easy to carry out, safe and reliable and highly efficient in terms of solvent consumption and production costs and thus is applicable to production of highly pure 4-hydroxyacetophenone on an industrial scale. Moreover, it was an object of the present invention to provide highly pure, crystalline, colorless and odorless 4-hydroxyacetophenone with superior (water) solubility and flowability properties.

Further objects underlying the present invention follow from the description below and the present patent claims.

According to a first aspect of the present invention, the stated objects are achieved by a method of purifying crude 4-hydroxyacetophenone, comprising or consisting of the following steps:
(a) Providing crude 4-hydroxyacetophenone,
(b) mixing the crude 4-hydroxyacetophenone of step (a) with one or a mixture of two or more solvent(s),
(c) optionally, heating the mixture obtained in step (b) to dissolve the 4-hydrwryacetophenone,
(d) optionally, adding an adsorbent, preferably activated carbon, to the mixture obtained in step (b) or step (c), if present,
(e) optionally, cooling the mixture obtained in step (b), step (c) or step (d), if present, to a temperature above the crystallization temperature of 4-hydrwryacetophenone,
(f) if step (d) is present, removing the adsorbent from the mixture of step (d) or step (e), if present, preferably by filtration,
(g) cooling of the mixture obtained in step (b) or step (c), if present, or further cooling of the mixture obtained in step (e), if step (d) is not present, or step (f), if present, to a temperature below the crystallization temperature of 4-hydroxyacetophenone to induce crystallization of 4-hydroxyacetophenone,
(h) collecting the crystallized 4-hydroxyacetophenone obtained in step (g),
optionally, carrying out the additional steps (i) to (k) once or several times:

(i) dissolving the crystallized 4-hydroxyacetophenone obtained in step (h) or a previous step (k), respectively, in one or a mixture of two or more solvent(s), optionally under heating, (j) cooling of the solution of step (i) to a temperature below the crystallization temperature of 4-hydroxyacetophenone to induce crystallization of 4-hydroxyacetophenone, (k) collecting the crystallized 4-hydroxyacetophenone obtained in step (j), (l) optionally, drying of the crystallized 4-hydroxyacetophenone obtained in step (h) or step (k), preferably until the total amount of the residual solvent(s) in the 4-hydroxyacetophenone is less than 10000 ppm, preferably 5000 ppm, preferably less than 2500 ppm, more preferably less than 1000 ppm, wherein the one solvent used in steps (b) and (i), if present, is independently selected from the group consisting of ethanol, cyclohexane, ethyl acetate, butyl acetate, diethyl carbonate and dimethyl carbonate or the two or more solvents of the mixture of two or more solvents used in steps (b) and (i), if present, are independently selected from the group consisting of ethanol, water, cyclohexane, ethyl acetate, butyl acetate, diethyl carbonate and dimethyl carbonate.

In the context of the own studies underlying the present invention, it was surprisingly found that if the method as defined above is used to purify crude 4-hydroxyacetophenone, highly pure and crystalline 4-hydroxyacetophenone with a purity of at least 90% (by weight), preferably of at least 91%, 92%, 93%, 94%, 95%, 96%, 97%, 98%, 99.0%, 99.1%, 99.2%, 99.3%, 99.4%, 99.5%, 99.6%, 99.7%, 99.8%, 99.90%, 99.91%, 99.92%, 99.93%, 99.94%, 99.95%, 99.96%, 99.97%, 99.98% or 99.99%, and with superior properties in terms of (whiter) color, less or more pleasant odor, better flowability and/or better solubility, preferably better solubility in water, and/or with a phenol content of less than 100 ppm (i.e. the amount of the residual phenol being less than 100 ppm) is obtained. Thus, the method as defined above is particularly advantageous since the product (crystallized 4-hydroxyacetophenone) obtained or obtainable by the method as defined above is suitable for and easier to use in cosmetic applications.

Suitable adsorbents that may be added in step (d) of the method as defined above, preferably for decolorization and/or deodorization, such as for example activated carbon or molecular sieves, depend on the nature of the selected solvent(s) and are known to the person skilled in the art.

A preferred embodiment according to the invention is a method as defined above, wherein in step (h) the collection of the crystallized 4-hydroxyacetophenone obtained in step (g) is carried out by means of centrifugation and/or decantation and/or filtration.

Another preferred embodiment according to the invention is a method as defined above, wherein in step (i) after dissolving the crystallized 4-hydroxyacetophenone obtained in step (h) or a previous step (k), respectively, in one or a mixture of two or more solvent(s) as defined above, optionally under heating, any residual insoluble impurities are removed, preferably by filtration.

Another preferred embodiment according to the invention is a method as defined above, wherein in step (k) the collection of the crystallized 4-hydroxyacetophenone obtained in step (j) is carried out by means of centrifugation and/or decantation and/or filtration. Preferably the crystallized 4-hydroxyacetophenone obtained after the centrifugation and/or decantation and/or filtration carried out in step (k) is washed with a small amount of the solvent(s) as defined above and collected by means of an additional step of centrifugation and/or decantation and/or filtration. More preferably, the filtrates obtained in step (k) after collecting the 4-hydroxyacetophenone are combined and subjected to another cooling and recrystallization step to achieve a maximal product yield.

A method according to the invention as defined above combining the use of the solvent(s) as defined above with the use of an adsorbent, such as activated carbon, preferably for decolorization and deodorization, during the recrystallization of 4-hydroxyacetophenone is particularly advantageous, yielding crystalline 4-hydroxyacetophenone with a purity of at least 90% (by weight), preferably of at least 91%, 92%, 93%, 94%, 95%, 96%, 97%, 98%, 99.0%, 99.1%, 99.2%, 99.3%, 99.4%, 99.5%, 99.6%, 99.7%, 99.8%, 99.90%, 99.91%, 99.92%, 99.93%, 99.94%, 99.95%, 99.96%, 99.97%, 99.98% or 99.99%.

Methods to determine the purity of chemical compounds are known to the person skilled in the art and can be selected appropriately depending on the respective requirements. In the context of the present invention, the method as defined above necessarily comprises or consists of the steps (a), (b), (g) and (h), and optionally additionally comprises steps (c) and/or (d) and/or (e) and/or (f) and/or (i) and/or (j) and/or (k) and/or (l). If step (d), the addition of the adsorbent, is comprised in the method as defined above, then step (f), the removal of the adsorbent, necessarily has to be present. Preferably, the method as defined above comprises or consists of all of the steps (a) to (l).

A further preferred embodiment according to the invention is a method as defined above, comprising or consisting of all of the steps (a) to (l), wherein steps (i) to (k) are carried out once or preferably twice, three, four or more times.

Another preferred embodiment according to the invention is a method as defined above, wherein in step (b) the crude 4-hydroxyacetophenone of step (a) is mixed with one solvent as defined above and wherein step (i) to (k) are present and wherein in step (i) the crystallized 4-hydroxyacetophenone obtained in step (h) is dissolved in one solvent as defined above (which can be the same or a different solvent as the one used in step (b)). A further preferred embodiment according to the invention is a method as defined above, wherein in step (i) a different solvent is used than in step (b).

Another preferred embodiment according to the invention is a method as defined above, wherein in step (b) the crude 4-hydroxyacetophenone of step (a) is mixed with a mixture of two solvents as defined above and wherein step (i) to (k) are present and wherein in step (i) the crystallized 4-hydroxyacetophenone obtained in step (h) is also dissolved in a mixture of two solvents as defined above (which can be the same mixture or a different mixture of solvents as the one used in step (b)). A further preferred embodiment according to the invention is a method as defined above, wherein in step (i) a different mixture is used than in step (b).

Another preferred embodiment according to the invention is a method as defined above, wherein in step (b) the crude 4-hydroxyacetophenone of step (a) is mixed with one solvent as defined above and wherein step (i) to (k) are present and wherein in step (i) the crystallized 4-hydroxyacetophenone obtained in step (h) is dissolved in a mixture of two solvents as defined above.

Another preferred embodiment according to the invention is a method as defined above, wherein in step (b) the crude 4-hydroxyacetophenone of step (a) is mixed with a mixture of two solvents as defined above and wherein step (i) to (k)

are present and wherein in step (i) the crystallized 4-hydroxyacetophenone obtained in step (h) is dissolved in one solvent as defined above.

Another preferred embodiment according to the invention is a method as defined above, wherein in step (b) the crude 4-hydroxyacetophenone of step (a) is mixed with ethanol/water, preferably 20 to 40 wt. % of ethanol in water, most preferably 25 to 30 wt. %, e.g. 28 wt. %, of ethanol in water and wherein step (i) to (k) are present and wherein in step (i) the crystallized 4-hydroxyacetophenone obtained in step (h) is dissolved in a mixture of ethanol/water, preferably in 20 to 40 wt. % of ethanol in water, most preferably in 25 to 30 wt. %, e.g. 28 wt. %, of ethanol in water.

Another preferred embodiment according to the invention is a method as defined above, wherein in step (b) the crude 4-hydroxyacetophenone of step (a) is mixed with dimethyl carbonate/cyclohexane, preferably 10 to 100 wt. % of dimethyl carbonate in cyclohexane, more preferably 50 to 75 wt. % of dimethyl carbonate in cyclohexane, more preferably 65 to 68 wt. % of dimethyl carbonate in cyclohexane, most preferably 67 wt. % of dimethyl carbonate in cyclohexane and wherein step (i) to (k) are present and wherein in step (i) the crystallized 4-hydroxyacetophenone obtained in step (h) is dissolved in a mixture of dimethyl carbonate/cyclohexane, preferably in 10 to 100 wt. % of dimethyl carbonate in cyclohexane, more preferably in 50 to 75 wt. % of dimethyl carbonate in cyclohexane, more preferably in 65 to 68 wt. % of dimethyl carbonate in cyclohexane, most preferably in 67 wt. % of dimethyl carbonate in cyclohexane.

Another preferred embodiment according to the invention is a method as defined above, wherein in step (b) the crude 4-hydroxyacetophenone of step (a) is mixed with ethanol and wherein step (i) to (k) are present and wherein in step (i) the crystallized 4-hydroxyacetophenone obtained in step (h) is dissolved in a mixture of dimethyl carbonate/cyclohexane, preferably in 10 to 100 wt. % of dimethyl carbonate in cyclohexane, more preferably in 50 to 75 wt. % of dimethyl carbonate in cyclohexane, more preferably in 65 to 68 wt. % of dimethyl carbonate in cyclohexane, most preferably in 67 wt. % of dimethyl carbonate in cyclohexane.

Another preferred embodiment according to the invention is a method as defined above, wherein in step (b) the crude 4-hydroxyacetophenone of step (a) is mixed with dimethyl carbonate/cyclohexane, preferably 10 to 100 wt. % of dimethyl carbonate in cyclohexane, more preferably 50 to 75 wt. % of dimethyl carbonate in cyclohexane, more preferably 65 to 68 wt. % of dimethyl carbonate in cyclohexane, most preferably 67 wt. % of dimethyl carbonate in cyclohexane and wherein step (i) to (k) are present and wherein in step (i) the crystallized 4-hydroxyacetophenone obtained in step (h) is dissolved in ethanol.

Another preferred embodiment according to the invention is a method as defined above, wherein in step (b) the crude 4-hydroxyacetophenone of step (a) is mixed with ethanol and wherein step (i) to (k) are present and wherein in step (i) the crystallized 4-hydroxyacetophenone obtained in step (h) is dissolved in a mixture of dimethyl carbonate/cyclohexane, preferably in 10 to 100 wt. % of dimethyl carbonate in cyclohexane, more preferably in 50 to 75 wt. % of dimethyl carbonate in cyclohexane, more preferably in 65 to 68 wt. % of dimethyl carbonate in cyclohexane, most preferably in 67 wt. % of dimethyl carbonate in cyclohexane.

The use of suitable (organic) solvents as defined above in the method as defined above is particularly advantageous, since it enables the purification method to be carried out at gentle temperatures and improves the flowability of the solution of 4-hydroxyacetophenone as well as the flowability of the crystallized 4-hydroxyacetophenone. Following the method as defined above, the one or a mixture of two or more solvent(s) as defined above can be recovered and used repeatedly, which increases production effectiveness and reduces the costs of the purification procedure, and generally of the production procedure, of highly pure 4-hydroxyacetophenone. Since the method as defined above is safe, reliable, cost and material efficient, it is suitable for operation on an industrial scale.

A preferred embodiment according to the invention is a method as defined above, wherein the mixture of two or more solvent(s) used in steps (b) and (i), if present, independently comprises or consists of one of the following combinations:

ethanol/water, preferably with up to 90 wt. % of ethanol in water (i.e. a mixture of 90 wt. % of ethanol and 10 wt. % of water),
ethyl acetate/cyclohexane, preferably with 10 to 99.99 wt. % of ethyl acetate in cyclohexane,
dimethyl carbonate/cyclohexane, preferably with 10 to 99.99 wt. % of dimethyl carbonate in cyclohexane, more preferably with 50 to 75 wt. % of dimethyl carbonate in cyclohexane, most preferably with 65 to 68 wt. % of dimethyl carbonate in cyclohexane,
butyl acetate/cyclohexane, preferably with 10 to 99.99 wt. % butyl acetate in cyclohexane,
diethyl carbonate/cyclohexane, preferably with 10 to 99.99 wt. % of diethyl carbonate in cyclohexane.

Another preferred embodiment according to the invention is a method as defined above, wherein in step(s) (b) and/or (i), if present, independently 0.5 to 70 wt. %, preferably 1 to 60 wt. %, more preferably 5 to 50 wt. % of 4-hydroxyacetophenone, in each case based on the total weight of the mixture obtained in step (b) or step (i), respectively, are combined with the solvent or the mixture of two or more solvents.

Advantageously, 4-hydroxyacetophenone is mixed with one or a mixture of two or more solvent(s) as defined above in an amount such that good solubility of the 4-hydroxyacetophenone in the one or a mixture of two or more solvent(s) is achieved, preferably at room temperature and/or when the mixture is heated.

Another preferred embodiment according to the invention is a method as defined above, wherein in step (c), if present, the mixture obtained in step (b) is heated to reflux, preferably is heated to reflux for 1 min to 2 hours, more preferably is heated to reflux for 30 min to 1 hour.

Heating the mixture obtained in step (b) to reflux is particularly advantageous since it ensures that all of the 4-hydroxyacetophenone contained in the mixture is fully dissolved, which supports efficient purification of the material.

Another preferred embodiment according to the invention is a method as defined above, wherein in step (d), if present, 0.1 to 25 wt. %, preferably 0.1 to 10 wt. %, more preferably 0.5 to 5 wt. % of the adsorbent, based on the total weight of the mixture obtained in step (d), are added to the mixture obtained in step (b) or step (c), if present.

Advantageously, a sufficiently high amount of adsorbent, preferably of activated carbon, is added to achieve complete decolorization and/or deodorization of the 4-hydroxyacetophenone to be purified.

Another preferred embodiment according to the invention is a method as defined above, wherein in case step (c) is present, in step (e), if present, the mixture obtained in step (c) or step (d), if present, is cooled to a temperature of 30 to 125° C., preferably to a temperature of 50 to 100° C., more preferably to a temperature of 60 to 70° C.

If the mixture has been heated in step (c), especially if it has been heated to reflux, it is advantageous to cool down the mixture to a temperature above the crystallization point of the 4-hydroxyacetophenone in step (e), if present, for further handling such as for example for the removal of the adsorbent in step (f), if present. It is important to ensure that the temperature is kept above the crystallization point of 4-hydroxyacetophenone at this point (steps (e) and (f) of the method as defined above, if present) to avoid any losses of product yield.

Another preferred embodiment according to the invention is a method as defined above, wherein in step (g) the mixture obtained in step (b) or step (c), if present, or the mixture obtained in step (e), if step (d) is not present, or step (f), if present, or the solution obtained in step (i), if present, is cooled to a temperature of −10° C. to below room temperature, preferably to a temperature of 0 to 20° C., more preferably to a temperature of 5 to 10° C. to induce crystallization of the 4-hydroxyacetophenone.

The crystallization temperature of the 4-hydroxyacetophenone is dependent on the concentration of the 4-hydroxyacetophenone in the mixture as well as on the kind and concentration of solvent(s) and other contaminants, if applicable, in the mixture. The person skilled in the art will lower the temperature of the mixture appropriately until crystallization of 4-hydroxyacetophenone is observed.

Another preferred embodiment according to the invention is a method as defined above, wherein the drying of the crystallized 4-hydroxyacetophenone in step (l), if present, is carried out at reduced pressure, preferably using a rotary evaporator, preferably at a reduced pressure of 0.05 to 0.1 MPa, more preferably at a reduced pressure of 0.07 to 0.08 MPa, and/or wherein the drying of the crystallized 4-hydroxyacetophenone in step (l), if present, is carried out at a temperature of 50 to 100° C., preferably of 60 to 90° C., more preferably of 75 to 85° C. and/or wherein the drying time is between 1 and 48 hours, preferably 2 and 24 hours, more preferably is about 4 to 20 hours.

Following a drying method as defined above in step (l) of the method as defined above is particularly advantageous, since it ensures good flowability and avoids caking of the final product.

The present invention also relates to a product comprising or consisting of crystallized 4-hydroxyacetophenone and a solvent selected from the group consisting of ethanol, cyclohexane, ethyl acetate, butyl acetate, diethyl carbonate and dimethyl carbonate, or comprising or consisting of 4-hydroxyacetophenone and two or more solvents selected from the group consisting of ethanol, water, cyclohexane, ethyl acetate, butyl acetate, diethyl carbonate and dimethyl carbonate, the product being obtained or obtainable by a method as defined above.

The product obtained or obtainable by a method as defined above is particularly crystalline, colorless, odorless and/or pure, preferably has a purity of at least 90% (by weight), more preferably of at least 91%, 92%, 93%, 94%, 95%, 96%, 97%, 98%, 99.0%, 99.1%, 99.2%, 99.3%, 99.4%, 99.5%, 99.6%, 99.7%, 99.8%, 99.90%, 99.91%, 99.92%, 99.93%, 99.94%, 99.95%, 99.96%, 99.97%, 99.98% or 99.99%, and/or has superior flowability. The product obtained or obtainable by a method as defined above preferably is also particularly well soluble in water and mixtures of water (cf. Examples, section "3) Solubility test" below for details).

The product obtained or obtainable by a method as defined above preferably (also) has a phenol content of less than 100 ppm, based on the total weight of the product. Thus, the product obtained or obtainable as defined above is particularly advantageous since it is suitable for and easier to use in cosmetic applications.

In the context of the present invention, the residual solvent contained in the product obtained or obtainable by a method as defined above is any solvent selected from the group consisting of ethanol, cyclohexane, ethyl acetate, butyl acetate, diethyl carbonate and dimethyl carbonate, or is any binary, ternary, quaternary or higher mixture of solvents selected from the group consisting of ethanol, water, cyclohexane, ethyl acetate, butyl acetate, diethyl carbonate and dimethyl carbonate.

Another preferred embodiment according to the invention is a product as defined above, wherein the total amount of the solvent(s) contained in the product is less than 10000 ppm, preferably less than 5000 ppm, preferably less than 2500 ppm, most preferably less than 1000 ppm, based on the total amount of the product.

When the 4-hydroxyacetophenone is purified and dried according to the method defined above, particularly when it is dried according to step (l) of the method as defined above, the residual amount of solvent(s) as defined above contained in the purified 4-hydroxyacetophenone can be minimized to less than 10000 ppm, preferably to less than 5000 ppm, preferably to less than 2500 ppm, most preferably to less than 1000 ppm, based on the total amount of the product, thus leading to a product with a purity of at least 90% (by weight), more preferably of at least 91%, 92%, 93%, 94%, 95%, 96%, 97%, 98%, 99.0%, 99.1%, 99.2%, 99.3%, 99.4%, 99.5%, 99.6%, 99.7%, 99.8%, 99.90%, 99.91%, 99.92%, 99.93%, 99.94%, 99.95%, 99.96%, 99.97%, 99.98% or 99.99%.

Reducing the amount of residual solvent(s) in the purified 4-hydroxyacetophenone is particularly advantageous, since it minimizes the chemical and/or technical odor of the product and yields a particularly colourless product, thus making it more appealing to and particularly safe to use for the customer.

Another preferred embodiment according to the invention is a product as defined above, wherein the solvents contained in the product are or comprise (a) dimethyl carbonate, cyclohexane, water and ethanol or (b) dimethyl carbonate, cyclohexane and ethanol.

Another preferred embodiment according to the invention is a product as defined above, wherein the solvents contained in the product are or comprise (a) ethanol and water, (b) dimethyl carbonate and cyclohexane, (c) ethyl acetate and cyclohexane, (d) butyl acetate and cyclohexane or (e) diethyl carbonate and cyclohexane.

Preferred embodiments of the product according to the invention correspond to or can be derived from the preferred embodiments of the method according to the invention which are explained above or vice versa.

DETAILED DESCRIPTION OF EMBODIMENTS OF THE INVENTION

Figure 1:
FIG. 1 shows a photograph of purified 4-hydroxyacetophenone obtained by an exemplary preferred method according to the invention.

The invention will now be described in more detail hereinafter with references to the examples. Further aspects of the present invention are disclosed in the accompanying claims.

EXAMPLES

1) Purification Procedures

Example 1

100 kg of crude 4-hydroxyacetophenone are dissolved in 300 kg of 28 wt. % of ethanol in water, heated to 78° C. and refluxed for 30 minutes. Then the temperature is lowered to 65° C. and 2 kg of activated carbon are added. Mix for 30 minutes. The activated carbon is removed by filtration. Then the temperature of the filtrate is slowly lowered to 5° C. to induce crystallization of the 4-hydroxyacetophenone, and subsequently the filtrate is centrifuged to collect the crystallized, wet product.

To the above wet product 315 kg of 28 wt. % of ethanol in water are added and heated to 70° C. to obtain a clear solution. Any unsolved impurities, if applicable, are removed by filtration. The temperature of the filtrate is slowly lowered to 5° C. to induce crystallization of the 4-hydroxyacetophenone, then the filtrate is centrifuged to separate the precipitated 4-hydroxyacetophenone. After removal of the supernatant, a small quantity of 28 wt. % of ethanol in water is used to wash the crystallized 4-hydroxyacetophenone. The collected washing solution and decanted supernatant were combined and used for another crystallization step to obtain maximum product yield.

The wet, fine product obtained above was transferred into a rotary evaporator, a vacuum of 0.07-0.08 MPa was applied, slowly heated to 75° C. and the product dried for 20 hours. 80 kg of the final product in the form of white, crystalline 4-hydroxyacetophenone were obtained. Purity: 99.92%, melting point: 109.3-109.7° C.

Example 2

100 kg of crude 4-hydroxyacetophenone are dissolved in 200 kg of 67 wt. % of dimethyl carbonate in cyclohexane, heated to 75° C. and refluxed for 30 minutes. Then the temperature is lowered to 70° C. and 2 kg of activated carbon are added. Mix for 30 minutes. The activated carbon is removed by filtration. Then the temperature of the filtrate is slowly lowered to 10° C. to induce crystallization of the 4-hydroxyacetophenone, and subsequently the filtrate is centrifuged to collect 80 kg of the crystallized, wet product.

The 80 kg of crystallized, wet product obtained above are added to 150 kg of dimethyl carbonate/cyclohexane (100 kg dimethyl carbonate and 50 kg cyclohexane) and the mixture is heated to 60° C. to obtain a clear solution. Any unsolved impurities, if applicable, are removed by filtration. The temperature of the filtrate is slowly lowered to 10° C. to induce crystallization of the 4-hydroxyacetophenone, then the filtrate is centrifuged to separate the precipitated 4-hydroxyacetophenone. After removal of the supernatant, a small quantity 67 wt. % of dimethyl carbonate in cyclohexane is used to wash the crystallized 4-hydroxyacetophenone. The collected washing solution and decanted supernatant were combined and used for another crystallization step to obtain maximum product yield.

The wet, fine product obtained above was transferred into a rotary evaporator, a vacuum of 0.07-0.08 MPa was applied, slowly heated to 75° C. and the product dried for 4 hours. 60 kg of the final product were obtained in the form of white, crystalline 4-hydroxyacetophenone. Purity: 99.98%, melting point: 109.5-109.9° C.

2) General Properties

Figure 2:
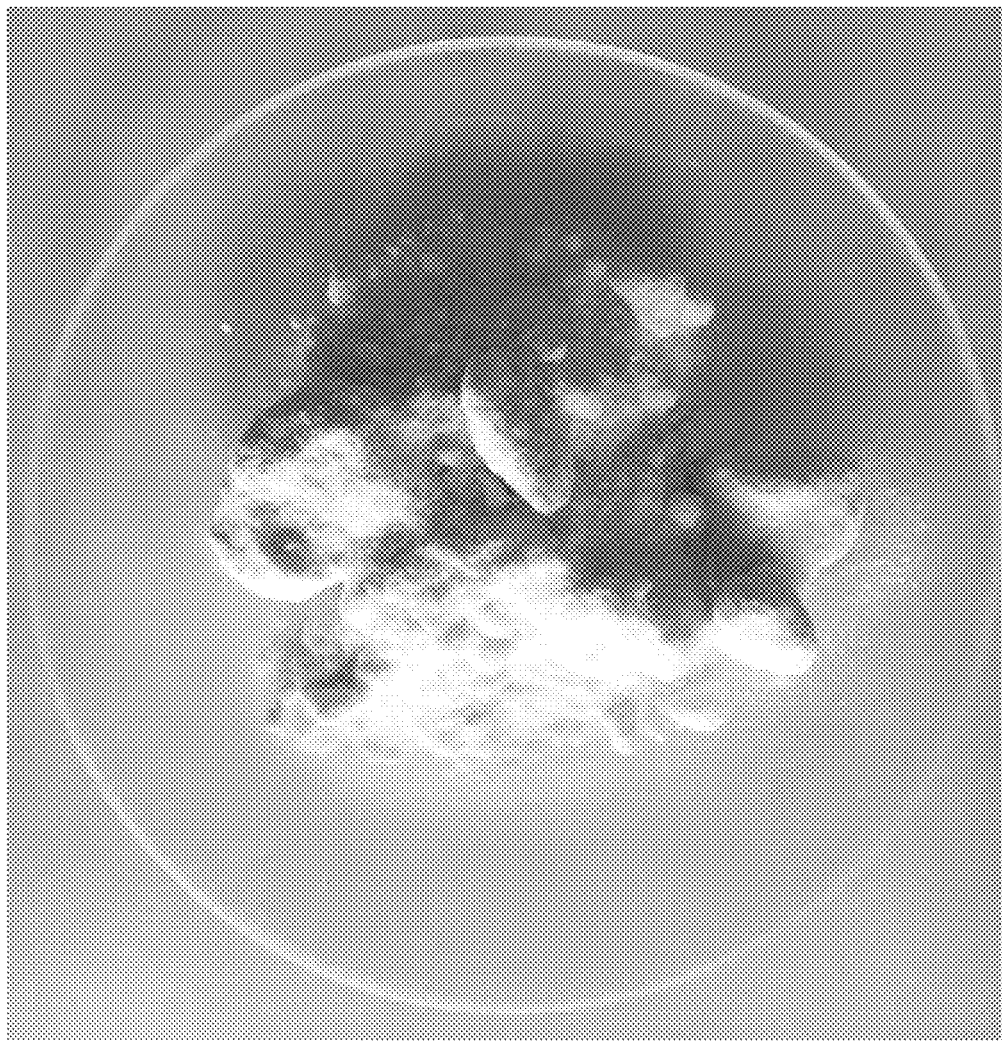
FIG. 2 shows a photograph of purified 4-hydroxyacetophenone obtained by an exemplary method according to the invention.

Description of the properties of the two batches of 4-hydroxyacetophenone depicted in FIG. 1 (in the following: Example 3) and FIG. 2 (in the following: Example 4):

Example 3: Small, shiny white crystals; lumps easily; looks very pure; when put into water, it distributes on the surface and slowly falls to the ground of the beaker Example 4: Grayish crystals with less shine; more powdery texture; forms more lumps; does not look as pure as Example 3; when put into water, it agglomerates and sinks to the ground 3) Solubility Tests The tests were carried out using the two batches of 4-hydroxyacetophenone (4-HAP) depicted in FIG. 1 (Example 3) and FIG. 2 (Example 4) with the aid of a magnetic stirrer and a stirring plate at room temperature (23° C., "cold water") or under heating (50° C., "warm water").

a) Test of 0.5 or 1.0 wt. % of 4-HAP in cold water:

0.5 wt. % 4-HAP:

Example 3 was completely dissolved after ca. 40 min and then stored (no crystallization/precipitation after 48 h of storage)

Example 4: After 50 min there were a few small lumps of solid left undissolved (not stored)

1 wt. % 4-HAP:

Neither Example 3 nor Example 4 was completely dissolved after 1 hour of stirring (not stored)

b) Test of 0.5 or 1.0 wt. % of 4-HAP in warm water:

0.5 wt. % and 1 wt. % 4-HAP:

Both Example 3 and Example 4 were solved completely after heating to 50° C. and cooling down while stirring (all test samples were stored at 5° C. and room temperature)

1 wt. % 4-HAP:

Example 4 crystallized at 5° C. after 24 h, Example 3 crystallized at 5° C. after 48 h c) Test of 0.5 or 1.0 wt. % of 4-HAP+3 wt. % 1,2-pentanediol (Hydrolite® 5)+5 wt. % glycerin in cold water:

0.5 wt. % 4-HAP:

Example 3 and Example 4 were solved completely after ca. 50 min and stored (crystallization/precipitation after 48 h of storage)

1 wt. % 4-HAP:

Example 4: After stirring for 60 min there were still a few lumps of solid left undissolved (not stored)

Example 3 was solved completely after ca. 50 min and stored (no crystallization/precipitation after 24 h of storage)

d) Test of 0.5 or 1.0 wt. % 4-HAP+3 wt. % 1,2-pentanediol (Hydrolite® 5)+5 wt. % glycerin in warm water:

0.5 and 1 wt. % of 4-HAP:

Both Example 3 and Example 4 were solved completely after heating up to 50° C. and cooling down while stirring (all test samples were stored at 5° C. and room temperature; no crystals after 24 h)

e) Test of 0.5 or 1.0 wt. % of 4-HAP+5 wt. % 1,2-pentanediol (Hydrolite® 5) in cold water:

0.5 wt. % of 4-HAP:

Example 3 was solved completely after ca. 50 min and stored (no crystallization/precipitation after 24 h of storage)

Example 4: After ca. 50 min there were a few little lumps of solid left undissolved (not stored)

1 wt. % of 4-HAP:

Example 3 was solved completely after ca. 50 min and stored (crystallization at 5° C. after 24 h of storage)

Example 4: After ca. 50 min there were lumps of solid left undissolved (not stored)

f) Test of 0.5 or 1.0 wt. % of 4-HAP+5 wt. % 1,2-pentanediol (Hydrolite® 5) in warm water:

0.5 and 1 wt. % 4-HAP:

Both Example 3 and Example 4 were solved completely after heating up to 50° C. and cooling down while stirring (all test samples were stored at 5° C. and room temperature)

1 wt. % 4-HAP:

Both Example 3 and Example 4 crystallized at 5° C. after 24 h of storage.

The invention claimed is:

1. A method of purifying crude 4-hydroxyacetophenone comprising:
   (a) providing crude 4-hydroxyacetophenone,
   (b) mixing the crude 4-hydroxyacetophenone of step (a) with one or more solvent(s) to obtain a mixture,
   (c) optionally, heating the mixture obtained in step (b) to dissolve the 4-hydroxyacetophenone,
   (d) optionally, adding an adsorbent to the mixture of step (b) or step (c), if present,
   (e) optionally, cooling the mixture of step (b), step (c) or step (d), if present, to a temperature above the crystallization temperature of 4-hydroxyacetophenone,
   (f) if step (d) is present, removing the adsorbent from the mixture of step (d) or step (e), if present,
   (g) cooling of the mixture of step (b) or step (c), if present, or further cooling of the mixture obtained in step (e), if step (d) is not present, or step (f), if present, to a temperature below the crystallization temperature of 4-hydroxyacetophenone to induce crystallization of 4-hydroxyacetophenone and to obtain crystallized 4-hydroxyacetophenone,
   (h) collecting the crystallized 4-hydroxyacetophenone, optionally, carrying out steps (i) to (k) one or more times:
   (i) dissolving the crystallized 4-hydroxyacetophenone of step (h) or step (k) in one or more solvent(s), optionally under heating, to produce a solution,
   (j) cooling of the solution of step (i) to a temperature below the crystallization temperature of 4-hydroxyacetophenone to induce crystallization of 4-hydroxyacetophenone and to obtain crystallized 4-hydroxyacetophenone,
   (k) collecting the crystallized 4-hydroxyacetophenone obtained in step (j),
   (l) optionally, drying of the crystallized 4-hydroxyacetophenone of step (h) or step (k),
      wherein at least one of the solvent(s) used in steps (b) and (i), if present, is independently selected from cyclohexane, ethyl acetate, butyl acetate, diethyl carbonate and dimethyl carbonate.

2. The method according to claim 1, wherein the one or more solvent(s) used in steps (b) and (i), if present, independently comprise one of the following combinations:
   ethanol/water,
   ethyl acetate/cyclohexane,
   dimethyl carbonate/cyclohexane,
   butyl acetate/cyclohexane, or
   diethyl carbonate/cyclohexane.

3. The method according to claim 1, wherein in step(s) (b) and/or (i), if present, independently 0.5 to 70 wt. % of 4-hydroxyacetophenone, based on the total weight of the mixture obtained in step (b) or step (i), respectively, is combined with the one or more solvent(s).

4. The method according to claim 1, wherein in step (c), the mixture obtained in step (b) is heated to reflux.

5. The method according to claim 1, wherein in step (d), 0.1 to 25 wt. %, of the adsorbent, based on the total weight of the mixture of step (d), is added to the mixture of step (b) or step (c), if present.

6. The method according to claim 1, wherein when step (c) and step (e) are present, in step (e) the mixture of step (c) or step (d), if present, is cooled to a temperature of 30 to 125° C.

7. The method according to claim 1, wherein in step (g) the mixture of step (b) or step (c), if present, or the mixture of step (e), if step (d) is not present, or step (f), if present, or the solution obtained in step (i), if present, is cooled to a temperature of −10° C. to below room temperature.

8. The method according to claim 1, wherein the drying of the crystallized 4-hydroxyacetophenone in step (1), if present, is carried out at reduced pressure, and at a temperature of 50 to 100° C., and wherein the drying time is between 1 and 48 hours.

9. A product consisting of crystallized 4-hydroxyacetophenone and one of the following:
   a solvent selected from cyclohexane, ethyl acetate, butyl acetate, diethyl carbonate and dimethyl carbonate, or
   two or more solvents each independently selected from ethanol, water, cyclohexane, ethyl acetate, butyl acetate, diethyl carbonate and dimethyl carbonate,
   wherein the product is obtained by a method according to claim 1.

10. A product according to claim 9, wherein the total amount of the solvent(s) contained in the product is less than 10000 ppm.

11. A product according to claim 9 wherein the solvents contained in the product are chosen from:
   (a) dimethyl carbonate, cyclohexane, water and ethanol, or
   (b) dimethyl carbonate, cyclohexane and ethanol.

12. A product according to claim 10, wherein the solvents contained in the product are chosen from:
   (a) ethanol and water,
   (b) dimethyl carbonate and cyclohexane,
   (c) ethyl acetate and cyclohexane,
   (d) butyl acetate and cyclohexane, and
   (e) diethyl carbonate and cyclohexane.

13. The method of claim 1, wherein the crystallized 4-hydroxyacetophenone obtained in step (h) or step (k) are dried until the total amount of the residual solvent(s) in the 4-hydroxyacetophenone is less than 10000 ppm.

14. The method of claim 13, wherein the crystallized 4-hydroxyacetophenone is dried until the total amount of the residual solvent(s) in the 4-hydroxyacetophenone is less than 10000 ppm.

15. The method of claim 13, wherein the crystallized 4-hydroxyacetophenone is dried until the total amount of the residual solvent(s) in the 4-hydroxyacetophenone is less than 5000 ppm.

16. The method of claim 13, wherein the crystallized 4-hydroxyacetophenone is dried until the total amount of the residual solvent(s) in the 4-hydroxyacetophenone is less than 2500 ppm.

17. The method of claim 13, wherein the crystallized 4-hydroxyacetophenone is dried until the total amount of the residual solvent(s) in the 4-hydroxyacetophenone is less than 1000 ppm.

18. The method of claim 1, wherein when two or more solvents are used in steps (b) and (i), if present, each of the two or more solvents are independently selected from the group consisting of ethanol, water, cyclohexane, ethyl acetate, butyl acetate, diethyl carbonate and dimethyl carbonate.

19. The method of claim 1, wherein 0.1 to 10 wt. % of the adsorbent, based on the total weight of the mixture obtained in step (d) is added to the mixture obtained in step (b) or step (c), if present.

20. The method of claim 7, wherein in step (g) the mixture obtained in step (b) or step (c), if present, or the mixture obtained in step (e), if step (d) is not present, or step (f), if present, or the solution obtained in step (i), if present, is cooled to a temperature to a temperature of 0 to 20° C.

* * * * *